US011821022B2

(12) United States Patent
McKinlay et al.

(10) Patent No.: US 11,821,022 B2
(45) Date of Patent: *Nov. 21, 2023

(54) ETHYLENE OXIDE ABSORPTION LAYER FOR ANALYTE SENSING AND METHOD

(71) Applicant: Medtronic MiniMed, Inc., Northridge, CA (US)

(72) Inventors: Robert McKinlay, Northridge, CA (US); Chi-En Lin, Northridge, CA (US); Tri T. Dang, Northridge, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 804 days.

This patent is subject to a terminal disclaimer.

(21) Appl. No.: 16/725,957

(22) Filed: Dec. 23, 2019

(65) Prior Publication Data

US 2021/0189450 A1 Jun. 24, 2021

(51) Int. Cl.
    *C12Q 1/00* (2006.01)
    *A61L 2/20* (2006.01)
    *A61L 2/232* (2006.01)
    *C12Q 1/32* (2006.01)

(52) U.S. Cl.
    CPC ............. *C12Q 1/006* (2013.01); *A61L 2/206* (2013.01); *A61L 2/232* (2013.01); *C12Q 1/32* (2013.01)

(58) Field of Classification Search
    CPC ........ C12Q 1/001; C12Q 1/004; C12Q 1/005; C12Q 1/006
    See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |

(Continued)

FOREIGN PATENT DOCUMENTS

| CA | 2667767 A1 * | 4/1999 | ............. C12Q 1/004 |
|---|---|---|---|
| WO | WO-2021250527 A1 * | 12/2021 | ......... A61B 5/14532 |

OTHER PUBLICATIONS

PCT International Search Report and Written Opinion dated Mar. 31, 2021 (12 pages).

*Primary Examiner* — Thane Underdahl

(74) *Attorney, Agent, or Firm* — Gates & Cooper LLP

(57) ABSTRACT

An analyte biosensor is provided having an analyte biosensing layer and an ethylene oxide absorption layer. The ethylene oxide absorption layer is provided over the analyte biosensing layer. A method is also provided.

22 Claims, 5 Drawing Sheets

(56) References Cited

U.S. PATENT DOCUMENTS

| | | |
|---|---|---|
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0105176 A1* | 5/2007 | Ibey ............... C12Q 1/54 435/14 |
| 2007/0123819 A1 | 5/2007 | Mernoe et al. |
| 2010/0160861 A1 | 6/2010 | Causey, III et al. |
| 2012/0328473 A1 | 12/2012 | Thomas et al. |
| 2015/0122647 A1* | 5/2015 | Shah ............... G01N 27/3271 427/2.12 |
| 2015/0177177 A1 | 6/2015 | Liu |
| 2016/0249840 A1 | 9/2016 | Pesantez et al. |
| 2019/0241926 A1* | 8/2019 | McKinlay ......... A61B 5/6849 |

* cited by examiner

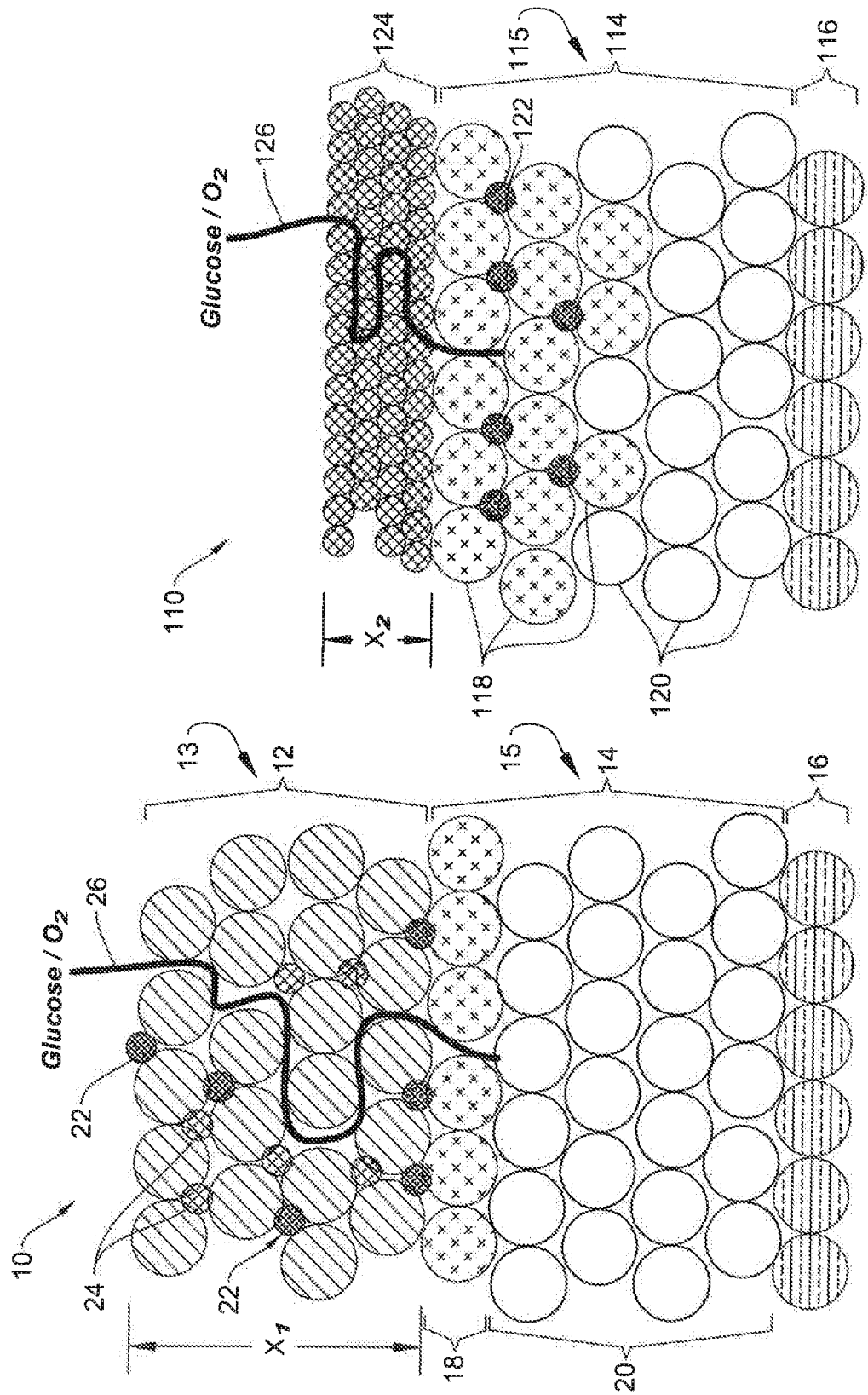

ETHYLENE OXIDE ABSORPTION LAYER FOR ANALYTE SENSING AND METHOD

CROSS REFERENCE TO RELATED APPLICATION

This application does not claim priority from any other application.

TECHNICAL FIELD

The subject matter of this application pertains to detection and concentration of analytes in mammals. More particularly, the subject matter relates to the sterilization of analyte sensors for use within a mammal.

BACKGROUND OF THE DISCLOSURE

Mammals are known to have cellular sensors that self-detect chemical constituents of the body, in particular tissues or blood, so that the body can control changes in constituent concentrations. However, disease and pathophysiological states can impart deviations from normal concentrations of constituents in bodily tissues and blood. Techniques are known for detecting blood glucose levels associated with diabetes. Further similar bodily malfunctions are also desired to be detected so that therapy and diagnostics can be implemented for patients. However, further improvements are needed to increase accuracy and longevity of inserted sensors when measuring constituents and physical membrane lamination and permeability issues can negatively affect performance.

Ethylene oxide (ETO) has been known to be a low temperature sterilant. However, improvements are needed in order to further protect the sterilization and operation of cellular sensors, or biosensors.

SUMMARY

A sensor sterilization absorption layer is provided for increasing sensing performance when measuring analytes, such as glucose, in the body of mammals that improves reliability and useable life over previously known techniques. A sterilization absorption layer is provided on a sensing element containing high density of functional groups able to bind ethylene oxide.

In one aspect, an analyte biosensor is provided having an analyte biosensing layer and an ethylene oxide absorption layer. The ethylene oxide absorption layer is provided over the analyte biosensing layer.

In another aspect, an analyte biosensing assembly is provided having an analyte biosensing layer and a sterilization absorption layer. The sterilization absorption layer is provided over the analyte biosensing layer.

In yet another aspect, a method is provided for sterilizing a biosensor. The method includes: providing an analyte biosensing layer and a sterilization absorption layer over the analyte biosensing layer; exposing the sterilization absorption layer to organic compounds comprising one of enzymes and proteins; and binding ethylene oxide with the sterilization absorption layer.

These and other aspects are contemplated and described herein. It will be appreciated that the foregoing summary sets out representative aspects of a system and method for detecting releasable coupling of a cap with an insulin delivery device and assists skilled readers in understanding the following detailed description.

BRIEF DESCRIPTION OF THE DRAWINGS

FIG. 1 is a diagrammatic cross-sectional view of an analyte biosensor having a sterilization absorption layer over an analyte biosensing layer.

FIG. 2 is a diagrammatic cross-sectional view of an analyte biosensor with a non-ethylene oxide binding layer over an analyte biosensing layer.

DETAILED DESCRIPTION OF THE EMBODIMENTS

Figure 3:
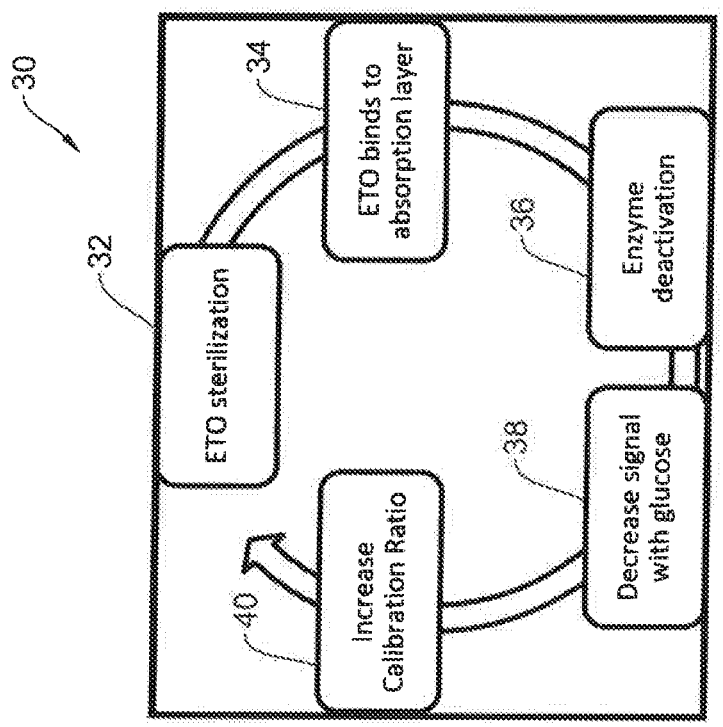
FIG. 3 is a simplified diagrammatic representation of an ethylene oxide (ETO) binding mechanism to glucose oxidase for a biosensor.

This disclosure is submitted in furtherance of the constitutional purposes of the U.S. Patent Laws "to promote the progress of science and useful arts" (Article 1, Section 8).

FIG. 1 is a diagrammatic cross-sectional view of an analyte biosensor 10 having a sterilization absorption layer 12 over an analyte biosensing layer 14, according to one implementation. More particularly, according to one implementation, the sterilization absorption layer 12 comprises an ethylene oxide (ETO) binding layer 13 and a non-ethylene oxide binding layer 24 having a layer thickness, $X_1$. The analyte biosensing layer 14 comprises a glucose oxidase (GOx) layer 15 comprising a deactivated glucose oxidase (GOx) layer 18 and an active glucose oxidase (GOx) layer 20. Sterilization absorption layer 12 enables passage of an interstitial fluid comprising a glucose and oxygen ($O_2$) mixture 26 through ethylene oxide (ETO) binding layer 13 from an in vivo exposure to tissue and/or bloods constituents where ethylene oxide 22 binds to ethylene oxide (ETO) binding layer 13 within sterilization absorption layer 12. Glucose and oxygen mixture 26 passes through a relatively thin deactivated glucose oxidase (GOx) layer 18 and into an active glucose oxidase (GOx) layer 20 where sensor 10 detects an electrical current that is proportional to the quantity of active glucose oxidase. Such detected capacitance change is provided below in further detail with reference to FIGS. 6 and 7 which enables detection of a specific biosensing state, or condition in such tissue and/or blood.

As shown in FIG. 1, analyte biosensing layer 14 includes a glucose oxidase (GOx) layer 15 comprising a relatively thin deactivated glucose oxidase (GOx) layer 18 proximate layer 12 and a relatively thick glucose oxidase (GOx) layer 20 beneath deactivated layer 18. Layer 20 is deposited atop a platinum layer, or surface 16. Optionally, any other suitable material, or metal layer, such as gold can be utilized in place of a platinum layer.

As detailed in FIG. 1, sterilization layer 12 and analyte biosensing layer 14 can be constructed with other optional components for sterilization layers and analyte biosensing layers including enzyme-based analyte sensing layers configured to detect one of: glucose, ketone, and lactate.

Such enzyme-based analyte sensing layer shown in FIG. 1 can be configured to realize glucose assay biosensing and comprises one of: glucose oxidase, glucose dehydrogenase, a modification of glucose oxidase, and a modification of glucose dehydrogenase. Such enzyme-based analyte sensing layer can be configured to realize ketone assay biosensing comprising 3-hydroxybutyrate dehydrogenase. Further, such enzyme-based analyte sensing layer can be configured to realize lactate assay biosensing comprising lactate dehydrogenase.

Such analyte biosensing layer of FIG. 1 can comprise a non-enzyme-based analyte sensing layer configured to detect glucose. Such non-enzyme-based analyte sensing layer can be configured to realize glucose assay biosensing comprising a boronic acid hydrogel.

Such ethylene oxide absorption layer of FIG. 1 can comprise a sterilization absorption layer over the analyte biosensing layer configured to preserve analyte sensing performance of the underlying ethylene oxide absorption layer. Such ethylene oxide absorption layer can also comprise a polymer with one of: a repeating amine; and one of a carboxyl acid group. Such ethylene oxide absorption layer can further also comprise one of: poly-l-lysine; chitosan, polyethyleneimine, and a protein (HSA).

Additionally, an adhesive layer can be provided at least in part by the ethylene oxide absorption layer, or binding layer 13 (of FIG. 1). As shown in FIG. 2, the ethylene oxide absorption layer itself can also provide the function of adhesion for layers 114 and 124.

Analyte biosensor 10 of FIG. 1 provides an analyte biosensing assembly including an analyte biosensing layer 14 and a sterilization layer 12 over the analyte biosensing layer 14. Such analyte biosensing layer of FIG. 1 can comprise an enzyme-based analyte sensing layer configured to detect one of: glucose, ketone, and lactate. Such sterilization absorption layer can comprise an ethylene oxide absorption layer comprising a high density of functional groups configured to bind with ethylene oxide. In such case, the functional groups can comprise a polymer with one of: a repeating amine; and one of a carboxyl acid group. Such sterilization absorption layer can comprise one of: poly-l-lysine; chitosan, polyethyleneimine, and a protein (HSA). Such sterilization absorption layer can comprise one of: linear molecules, branched molecules and dendrimer molecules. Such sterilization absorption layer can further comprise an adhesive layer. Such sterilization absorption layer can comprise a first region having a first thickness and a second region having a second thickness unique from the first thickness. Finally, such sterilization absorption layer can be provided with a thickness that provides a metering layer configured to control rate of transmission of analyte to the analyte biosensing layer.

Also according to FIG. 1, a method is provided for sterilizing a biosensor. The method includes: providing an analyte biosensing layer and a sterilization absorption layer over the analyte biosensing layer; exposing the sterilization absorption layer to organic compounds comprising one of enzymes and proteins; and binding ethylene oxide with the sterilization absorption layer. In one case, the analyte biosensing layer comprises an enzyme-based analyte sensing layer, and further comprising detecting at the analyte biosensing layer one of: glucose, ketone, and lactate. In one case, the sterilization absorption layer comprises an ethylene oxide absorption layer comprising a high density of functional groups configured to bind with ethylene oxide, and further comprising binding ethylene oxide with the functional groups. In such case, the functional groups can comprise a polymer with one of: a repeating amine; and one of a carboxyl acid group.

FIG. 2 is a diagrammatic cross-sectional view of an analyte biosensor 110 with a non-ethylene oxide binding layer 124 over an analyte biosensing layer 114, according to a non-preferred implementation. More particularly, non-ethylene oxide binding layer 124 is layered over analyte biosensing layer 114 comprising a glucose oxidase (GOx) layer 115 having a substantially thick deactivated glucose oxidase (GOx) layer 118 and into an active glucose oxidase (GOx) layer 120. Due to a lack of an ethylene oxide binding layer (such as layer 12 of FIG. 1), ethylene oxide 122 binds to glucose oxidase layer 118 which causes such deactivation and reduces accuracy of detected current changes in sensor 110 as activated glucose oxidase layer 120 is reduced in thickness over that shown in the implementation of FIG. 1. Non-ethylene oxide binding layer 124 has a layer thickness $X_2$ where $X_1$ is greater than $X_2$ due to the addition of an ETO-binding layer.

Figure 6:
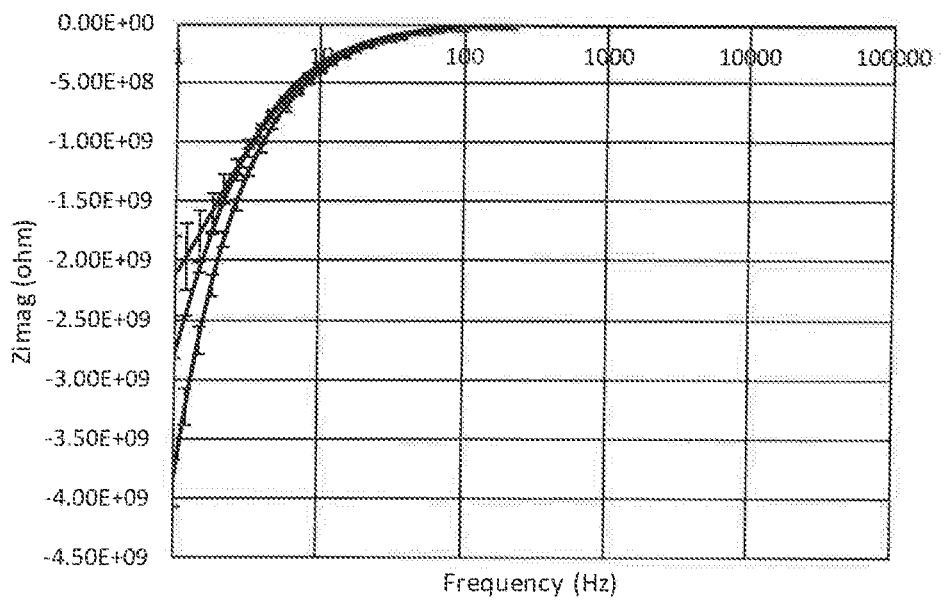
FIG. 6 is a plot of low, medium and high absorption layer mechanisms of electrochemical impedance (capacitance) versus frequency for a biosensor with exposure to ethylene oxide (ETO).
Figure 7:
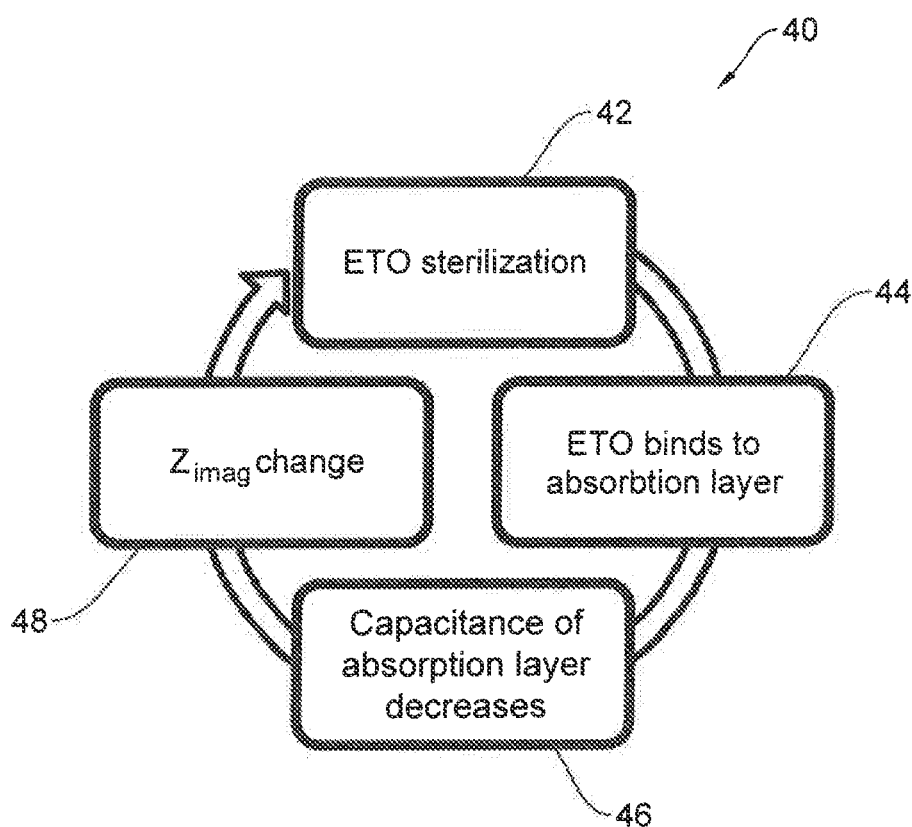
FIG. 7 is a simplified diagrammatic representation of an ethylene oxide (ETO) sterilization for a biosensor having a binding mechanism to an absorption layer for glucose oxidase.

As a result of the reduced thickness of activated glucose oxidase layer 120, sensor 120 is less able to accurately detect current by breaking down products generated by layer 120. FIGS. 6 and 7 below a different technique to measure the effort of ethylene oxide on protective/absorption layer that enables detection of a specific biosensing state, or condition in such tissue and/or blood. Layer 112 enables passage of a glucose and oxygen ($O_2$) mixture 26 through non-ethylene oxide binding layer 124 from an in vivo exposure to tissue and/or blood constituents where ethylene oxide 122 binds to glucose oxidase 118 in layer 114, causing deactivation. In operation, sensor 120 detects current by breaking down the products generated by layer 120. Therefore, if layer 120 is thinner or compromised, the current does not enable as accurate a detection of a specific biosensing state. Passage of glucose and oxygen mixture 26 into a thinner active glucose oxidase (GOx) layer 120 where sensor 120 detects an impedance, or capacitance as provided below in further detail with reference to FIGS. 6 and 7 does not enable as accurate a detection of a specific biosensing state, or condition in such tissue and/or blood. Layer 120 is deposited atop a platinum layer, or surface 116, but can optionally be provided atop a gold layer, or some other suitable metal layer.

FIG. 3 is a simplified diagrammatic representation of an ethylene oxide (ETO) binding mechanism 30 for binding to a glucose oxidase layer for a biosensor of FIG. 2 that does not have an absorption layer. More particularly, a first stage or step involves an ethylene oxide (ETO) sterilization Step 32. Secondly, ethylene oxide (ETO) binds to an absorption layer in step 34. Subsequently, an enzyme deactivation step 36 occurs which results in a decreased in layer 114 comprising layer 118 being deactivated. This deactivation of layer 118 results in a decreased signal with glucose 38 as shown in Step 38. Finally, an increased calibration ration is shown in Step 40 resulting from the enzyme deactivation of a portion 118 of the sensing layer provided by layer 114.

Figure 4:
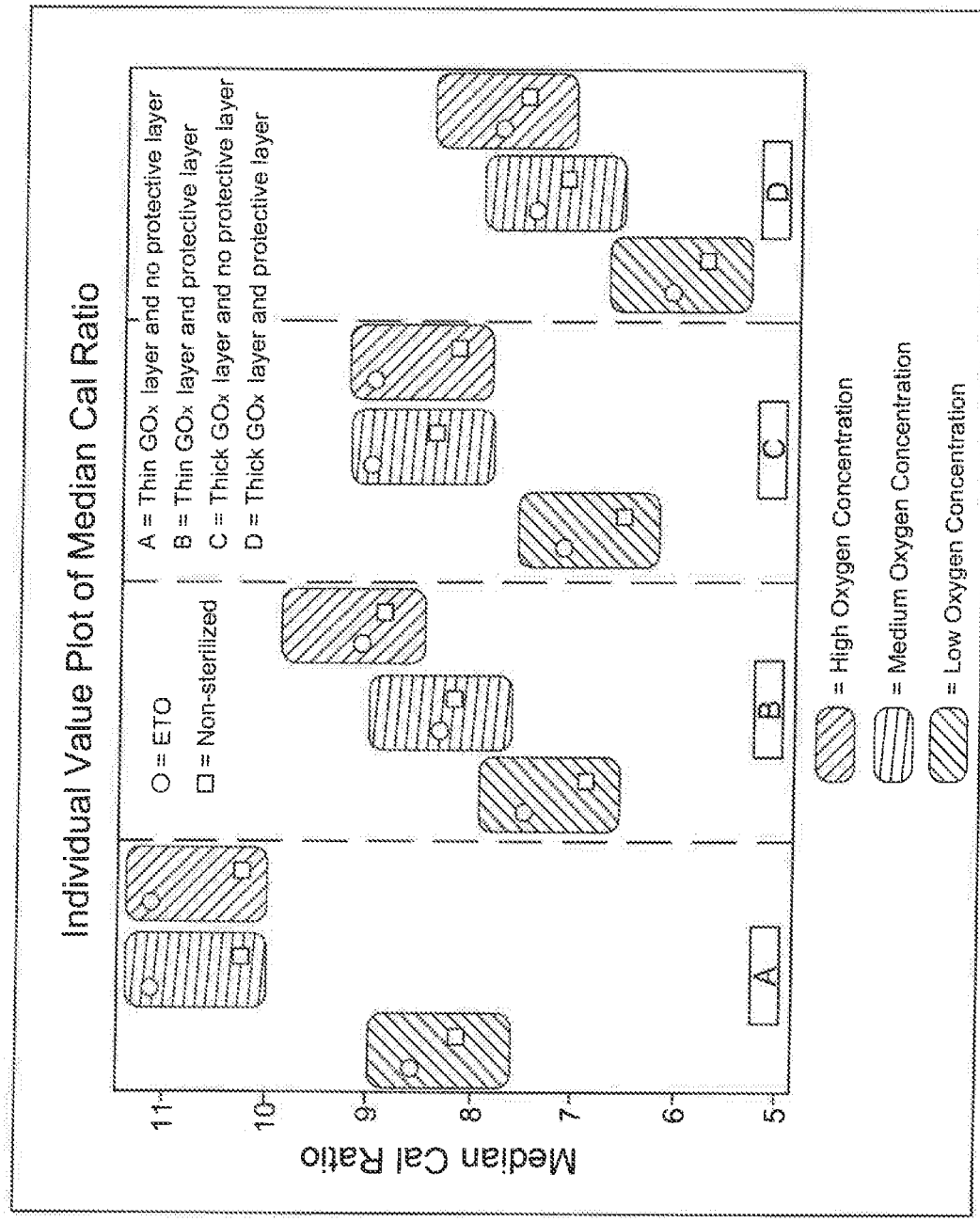
FIG. 4 is a diagrammatic plot of median calibration ratios of glucose concentration over sensor signal for both thin and thick glucose oxidase (GOx) layers both with and without a sterilization absorption layer.

FIG. 4 is a diagrammatic plot of median calibration ratios of glucose concentration over sensor signal for both thin and thick glucose oxidase (GOx) layers both with and without a sterilization absorption. Column A shows individual value plot of median calibration ratio for high oxygen concentration, medium oxygen concentration, and low oxygen concentration where there is a thin GOx layer and no protective layer over a sensor. Column B shows the same where there is a thin GOx layer and a protective layer over a sensor. Column C shows the same where there is a thick GOx layer and no protective layer over a sensor. Finally, Column D shows the same where there is a thick GOx layer and a protective layer over a sensor. The Median Calibration Ratio represents a ratio of the "glucose concentration" over the "sensor signal" that is detected as shown in FIG. 4.

Figure 5:
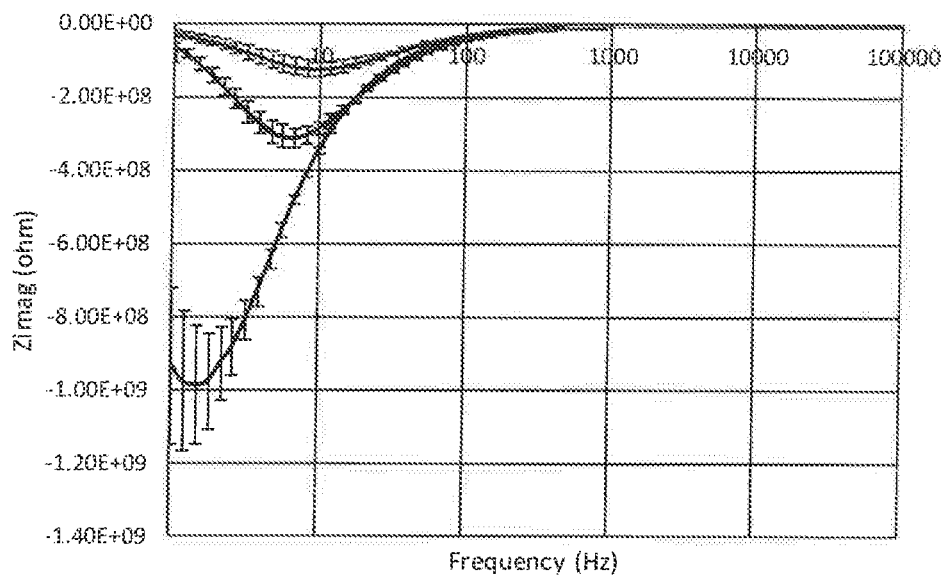
FIG. 5 is a plot of low, medium and high absorption layer mechanisms of electrochemical impedance (capacitance) versus frequency for a biosensor with no exposure to ethylene oxide (ETO).

FIGS. 5 and 6 result from an experiment using a sensor having a different sensor structure than that shown in FIGS. 1 and 2. More particularly, this sensor structure had an ETO binding layer (see layer 12, with a height of $X_1$) that was deposited onto a metal surface (see layer 16, with the material actually being gold). This tested sensor structure had three levels of height/thickness of layer 12 deposited onto layer 16. FIGS. 5 and 6 then compare the effect of ETO on layer 12. Essentially, this "electrical impedance" technique provides an actual proof of ETO binding to layer 12, by changing the resulting electrical impedance signature drastically. In essence, FIGS. 5 and 6 utilize this different sensor embodiment in order to support assertions made regarding FIGS. 1 and 2.

FIG. 5 is a plot of low, medium and high absorption layer mechanisms of electrochemical impedance (capacitance) versus frequency for a biosensor of FIG. 2 with exposure to ethylene oxide and having exposure to ethylene oxide (ETO) because there is no sterilization absorption layer.

FIG. 6 is a plot of low, medium and high absorption layer mechanisms of electrochemical impedance (capacitance) versus frequency for a biosensor of FIG. 1 with no exposure of ethylene oxide (ETO) where there is an ethylene oxide (ETO) binding layer that provides a protective layer. The sterilization absorption layer comprises an ETO binding layer which provides a protective layer over the biosensor.

FIG. 7 is a simplified diagrammatic representation of an ethylene oxide (ETO) sterilization process 40 for a biosensor having a binding mechanism to an absorption layer for glucose oxidase. More particularly, ethylene oxide (ETO) sterilization Step 42 precedes Step 44 where ETO binds to an absorption layer 12 (see FIG. 1). Step 44 depicts ETO 22 (see FIG. 1) bound to sterilization absorption layer 22. Subsequently, the resulting capacitance of the sterilization absorption layer 22 (see FIG. 1) decreases in Step 46. Subsequently, the impedance (or capacitance) $Z_{imag}$ changes due to the layer changing. As shown in FIG. 5, the absorption layer significantly changes capacitance with addition of the ETO absorption layer.

Pursuant to the process summarized in FIG. 7, the ethylene oxide absorption layer protects the underlying analyte biosensing layer. This underlying analyte biosensing layer may be enzyme based and/or non-enzyme based. Analytes include glucose, ketone, and lactate. Enzyme biosensing layer include examples such as glucose oxidase and/or glucose dehydrogenase and/or modification thereof for glucose assay biosensing for $1^{st}$ generation, $2^{nd}$ generation and $3^{rd}$ generation biosensing. Other enzyme biosensing layers include examples such as 3-hydroxybutyrate dehydrogenase and lactate dehydrogenase for ketone assay and lactate assay sensing. Non-enzyme biosensing layers include examples such as boronic acid hydrogels for glucose assay.

Ethylene oxide (ETO) creates alkylation reactions with organic compounds such as enzymes and other proteins. These reactions inactivate enzymes having sulfhydryl groups providing an effective sterilizing agent for both heat sensitive and moisture sensitive materials.

As shown in FIG. 4, provision of a sterilization absorption layer is configured to preserve analyte sensing performance from ethylene oxide. Analyte sensing can be glucose-based and/or other enzyme-based sensing platforms. The sterilization absorption layer is configured to contain high density of functional groups that are able to bind ethylene oxide, as shown in FIG. 5. Provision of a sterilization absorption layer comprised of a polymer with repeating amine and/or carboxylic acid groups is shown in FIG. 5 with a significantly decreased capacitance values for each range of layer thickness. The sterilization absorption layer can be poly-l-lysine, chitosan, polyethyleneimine, or proteins such as HSA. The sterilization absorption layer can be linear, branched, dendrimer. The material can act as both an adhesive layer and a sterilization absorption layer. Finally, the sterilization absorption layer can be different made with different thicknesses.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

While the subject matter of this application was motivated in addressing a glucose biosensor encasement, it is in no way so limited. The disclosure is only limited by the accompanying claims as literally worded, without interpretative or other limiting reference to the specification, and in accordance with the doctrine of equivalents. Other aspects and implementations of other biosensor encasements are contemplated.

In compliance with the statute, the various embodiments have been described in language more or less specific as to structural and methodical features. It is to be understood, however, that the various embodiments are not limited to the specific features shown and described, since the means herein disclosed comprise disclosures of putting the various embodiments into effect. The various embodiments are, therefore, claimed in any of its forms or modifications within the proper scope of the appended claims appropriately interpreted in accordance with the doctrine of equivalents.

What is claimed is:

1. An analyte biosensor, comprising:
   an analyte biosensing layer comprising a deactive top layer over an active analyte biosensing layer;
   wherein the analyte biosensing layer comprises an enzyme;
   wherein the deactivate top layer comprises the enzyme deactivated by reacting with ethylene oxide and the active analyte biosensing layer comprises the active enzyme; and
   an ethylene oxide absorption layer over the analyte biosensing layer proximate to the deactive top layer of the analyte biosensing layer.

2. The biosensor of claim 1, wherein the analyte biosensor detects an analyte by the reaction of the enzyme with these analyte(s),
   wherein the analyte is selected from the group comprising glucose, ketone, and lactate.

3. The biosensor of claim 2, wherein the enzyme of the analyte biosensing layer comprises one of: glucose oxidase, glucose dehydrogenase, a modification of glucose oxidase, and a modification of glucose dehydrogenase.

4. The biosensor of claim 2, wherein the enzyme of the analyte biosensing layer comprises 3-hydroxybutyrate dehydrogenase.

5. The biosensor of claim 2, wherein the enzyme of the analyte biosensing layer comprises lactate dehydrogenase.

6. The biosensor of claim 1, wherein the ethylene oxide absorption layer comprises a sterilization absorption layer over the analyte biosensing layer configured to preserve analyte sensing performance of the underlying ethylene oxide absorption layer.

7. The biosensor of claim 1, wherein the ethylene oxide absorption layer comprises a polymer with one of: a repeating amine; and one of a carboxyl acid group.

8. The biosensor of claim 1, wherein the ethylene oxide absorption layer comprises one of: poly-l-lysine; chitosan, polyethyleneimine, and a protein (HSA).

9. The biosensor of claim 7, wherein the ethylene oxide absorption layer further comprises an adhesive layer.

10. An analyte biosensing assembly, comprising:
an analyte biosensing layer comprising a deactive top layer over an active analyte biosensing layer;
wherein the analyte biosensing layer comprises and enzyme;
wherein the deactivate top layer comprises the enzyme deactivated by reacting with ethylene oxide and the active analyte biosensing layer comprises the active enzyme; and
a sterilization absorption layer over the analyte biosensing layer proximate the deactive top layer of the analyte biosensing layer.

11. The analyte biosensing assembly of claim 10, wherein the analyte biosensor detects an analyte by the reaction of the enzyme with these analyte(s), wherein the analyte is selected from the group comprising glucose, ketone, and lactate.

12. The analyte biosensing assembly of claim 10, wherein the sterilization absorption layer comprises an ethylene oxide absorption layer comprising a high density of functional groups configured to bind with ethylene oxide.

13. The analyte biosensing assembly of claim 12, wherein the functional groups comprise a polymer with one of: a repeating amine; and one of a carboxyl acid group.

14. The analyte biosensing assembly of claim 10, wherein the sterilization absorption layer comprises one of: poly-l-lysine; chitosan, polyethyleneimine, and a protein (HSA).

15. The analyte biosensing assembly of claim 10, wherein the sterilization absorption layer comprises one of: linear molecules, branched molecules and dendrimer molecules.

16. The analyte biosensing assembly of claim 10, wherein the sterilization absorption layer further comprises an adhesive layer.

17. The analyte biosensing assembly of claim 10, wherein the sterilization absorption layer comprises a first region having a first thickness and a second region having a second thickness unique from the first thickness.

18. The analyte biosensing assembly of claim 10, wherein a thickness of the sterilization absorption layer provides a metering layer configured to control rate of transmission of analyte to the analyte biosensing layer.

19. A method for sterilizing a biosensor, comprising:
providing an analyte biosensing layer comprising:
a) a top layer capable of being deactivated
b) an active analyte biosensing layer under the top layer of a) and
c) wherein the top layer a) and active analyte biosensing layer b) comprise an enzyme;
and a sterilization absorption layer over the analyte biosensing layer;
deactivating the enzyme of top layer of the analyte biosensing layer;
exposing the sterilization absorption layer to organic compounds comprising one of enzymes and proteins; and
binding ethylene oxide with the sterilization absorption layer.

20. The method of claim 19, wherein the analyte biosensing layer detects an analyte by the reaction of the enzyme with these analyte(s), wherein the analyte is selected from the group comprising glucose, ketone, and lactate.

21. The method of claim 19, wherein the sterilization absorption layer comprises an ethylene oxide absorption layer comprising a high density of functional groups configured to bind with ethylene oxide, and further comprising binding ethylene oxide with the functional groups.

22. The method of claim 21, wherein the functional groups comprise a polymer with one of: a repeating amine; and one of a carboxyl acid group.

* * * * *